United States Patent [19]

Davies

[11] Patent Number: 5,494,656
[45] Date of Patent: Feb. 27, 1996

[54] SECOND SPHERE COMPLEXES AS RELAXATION AGENTS FOR IMAGE ENHANCEMENT IN MAGNETIC RESONANCE IMAGING

[75] Inventor: Julian A. Davies, Toledo, Ohio

[73] Assignee: The University of Toledo, Toledo, Ohio

[21] Appl. No.: 406,356

[22] Filed: Mar. 17, 1995

Related U.S. Application Data

[63] Continuation of Ser. No. 121,227, Sep. 14, 1993, abandoned.
[51] Int. Cl.$^6$ ..................................................... A61B 5/055
[52] U.S. Cl. ........................ 424/9.364; 514/492; 514/502; 514/836; 556/50; 556/55; 556/63; 556/77; 556/105; 556/116; 556/134; 556/148; 534/15; 534/16; 436/173
[58] Field of Search .......................... 424/9.364; 514/492, 514/502, 836; 556/50, 55, 63, 77, 105, 116, 134, 148; 128/653.4, 654; 436/173; 534/15, 16

[56] References Cited

U.S. PATENT DOCUMENTS

| | | | |
|---|---|---|---|
| 4,880,008 | 11/1989 | Lauffer | 128/654 |
| 5,010,191 | 4/1991 | Englestad et al. | 544/225 |
| 5,225,282 | 7/1993 | Chagnon et al. | 428/407 |

OTHER PUBLICATIONS

Bagyinka et al. Chem. Abstracts, 88:116562f, (1978).
Rudzitis et al., Chem. Abstracts, 76:37921w, (1971).
Rajan et al., Chem. Abstracts, 85:56477h, (1976).

*Primary Examiner*—Gary E. Hollinden
*Attorney, Agent, or Firm*—Willian Brinks Hofer Gilson & Lione

[57] ABSTRACT

A second sphere contrast enhancing agent for magnetic resonance imaging comprises a paramagnetic metal ion having catecholate ligands coordinated thereto and having water molecules hydrogen bonded to the catecholate ligands.

12 Claims, No Drawings

5,494,656

SECOND SPHERE COMPLEXES AS RELAXATION AGENTS FOR IMAGE ENHANCEMENT IN MAGNETIC RESONANCE IMAGING

This application is a continuation of application Ser. No. 08/121,227, filed Sep. 14, 1993 abandoned.

FIELD OF THE INVENTION

This invention relates generally to second sphere complexes useful as relaxation agents for image enhancement in magnetic resonance imaging. More particularly, the invention is directed to second sphere complexes comprising paramagnetic metal ions having catecholate ligands coordinated thereto and having water molecules hydrogen bonded to said ligands, and to a method for performing magnetic resonance imaging of a patient using said second sphere complexes.

BACKGROUND OF THE INVENTION

Magnetic resonance imaging (MRI) is a nuclear magnetic resonance (NMR) technique which may be used clinically to differentiate between normal and abnormal tissues. The $^1H$ NMR imaging method is based upon differences in water proton concentrations and relaxation rates within different tissue types. The use of contrast agents such as paramagnetic metal chelates to enhance the diagnostic utility of MRI has only recently became practical.

U.S. Pat. No. 4,880,008 to Lauffer discloses in vivo enhancement of NMR relaxivity utilizing chelated paramagnetic ions such as iron(III) and gadolinium(III). The chelating substances include bis, tris, and tetracatechol compounds.

U.S. Pat. No. 5,010,191 to Engelstad et al. discloses imaging agents for in vivo magnetic resonance and scintigraphic imaging, including chelated transition metal and lanthanide metal complexes. The patent discloses a comparison screening protocol including the iron(III) chelate of TIRON®. However, the patent does not disclose the second sphere iron(III) complex of the salt of disodium-1,2-dihydroxybenzene-3,5-disulfonate having water molecules hydrogen bonded to the ligand groups.

SUMMARY OF THE INVENTION

Accordant with the present invention, second sphere complexes useful as relaxation agents for image enhancement in magnetic resonance imaging have surprisingly been discovered. These complexes include paramagnetic metal ions chelated with catecholate ligands, wherein water molecules are hydrogen bonded to the ligands. Also contemplated by the present invention is a method for magnetic resonance image enhancement utilizing said second sphere complexes.

DETAILED DESCRIPTION OF THE PREFERRED EMBODIMENT

The development of pharmaceutical agents which enhance image contrast between tissue types presents unique challenges since such agents are not themselves imaged but rather function through affecting water molecule proton relaxation rates. This important distinction between image contrast agents and other types of clinically useful diagnostic pharmaceuticals, such as for example X-ray contrast agents or radiopharmaceuticals, leads to major differences in the in vivo distribution requirements of each type of agent. Thus, for a magnetic resonance imaging contrast agent to be effective, it is not required that the agent localize in the target tissue, but rather that the water proton relaxation rate in the target tissue be affected differently from the relaxation rate of the water protons in the surrounding tissue. Such differentiation without preferential localization of the contrast agent is possible because of the mode of action of these image enhancement agents.

Paramagnetic species, such as certain complexes of memal ions, can alter the longitudinal and/or transverse relaxation rates of adjacent nuclei by dipolar interactions. The metal ions with the most suitable magnetic moments and relaxation efficiencies for this purpose are gadolinium(III) and iron(III). In order for the metal ion to enhance the relaxation rate of water protons in tissue, it is important that the water molecules approach close to the paramagnetic center. It is believed that three basic types of interactions between the metal ion and water molecules may occur. In an inner sphere interaction, water molecules bind to and exchange with the metal ion, for a very effective contact. In an outer sphere interaction, all of the metal ion coordination sites are occupied by a set of ligands, and so water molecules are affected only through translational diffusion past the paramagnetic center. In an intermediate case, i.e., second sphere interaction, the metal ion is surrounded by a set of ligands which prevent direct coordination of water molecules to the metal ion. However, the ligands of a second sphere complex also provide bonding sites for the hydrogen bonding of water molecules thereto.

Metal ions which interact with water molecules by an inner sphere mechanism are very effective for enhancing relaxation rates, but such ions generally exhibit very high toxicities. The origin of this toxicity lies in the availability of coordination sites at the metal ion center which leads to binding by not only water molecules but also by activated oxygen, nitrogen, or sulfur groups of a lumber of biomolecules. The coordination sites at the metal center can essentially be removed by using a suitable set of ligands. However, although this reduces toxicity, it typically leaves only the less-effective outer sphere interactions with water molecules to provide relaxation rate enhancement. To balance these effects, complexes designed to operate by second sphere interactions have been developed herein for use in magnetic resonance imaging.

The ligands useful for second sphere relaxation enhancement must meet specific requirements. They must bind strongly to paramagnetic metal ions, since ligand dissociation would result in metal ion toxicity and ligand-derived organic toxicity. Useful ligands must form complexes which are excreted efficiently to prevent long term toxicity by, for example, the accumulation of lipophilic complexes in membranes or retention by cells in the reticular endothelial system. Moreover, the useful ligands must provide sites for the hydrogen bonding of water molecules.

The requirement for strong paramagnetic metal ion-to-ligand binding is well understood. Thus, the diethylenetriaminepentaacetic acid complex of gadolinium(III), with an association constant K(ML) of 22.5, is excreted intact and so exhibits a low toxicity. However, the analogous ethylenediaminetetraacetic acid complex of gadolinium(III) with an association constant K(ML) of 17.35 exhibits a toxicity comparable to the free, aqueous gadolinium(III) ion, thereby suggesting in vivo dissociation.

The mechanism of efficient excretion of the complexes from the body, which preferably should occur within a few hours following administration, is less-well understood. Only certain broad principles are available to assist in the complex design. Thus, the presence of highly charged and/or hydrogen bonded groups and the absence of lipophilic side chains minimizes interactions with membranes, plasma proteins, etc., and so allows for effective renal excretion. Certain anionic complexes are excreted by the hepatobiliary pathway in competition with excretion via the kidneys. Although poorly understood, excretion via the liver may involve transport of anionic complexes by the same agents that transport fatty acids, bile acids, and heme degradation products. Thus, for efficient excretion to avoid long term toxicity, the factors promoting both renal and hepatobiliary pathways must be maximized.

The presence of hydrogen bonded water molecules is critical to the operability and utility of second sphere relaxation complexes, according to the present invention. Complexes which fall into this group rely on the hydrogen bonding of water molecules to the heteroatoms which form the paramagnetic metal ion-to-ligand linkages.

The second sphere complexes of the present invention comply with the requirements set forth above. The inventive complexes are prepared utilizing paramagnetic metal ions, which are detectable in their chelated form by magnetic resonance imaging, such as, for example, iron(III), gadolinium(III), manganese (II and III), chromium(III), copper(II), dysprosium(III), terbium(III), holmium (III), erbium (III), and europium (III) . Preferred paramagnetic metal ions comprise iron(III) and gadolinium(III).

Suitable ligands for preparing the second sphere complexes according to the present invention include catecholate systems prepared from, for example, derivatives of 1,2-benzenediol (catechol) such as the salt disodium-1,2-dihydroxybenzene-3,5-disulfonate. A preferred ligand comprises the salt disodium-1,2-dihydroxybenzene-3,5-disulfonate. The pendant sulfonate groups act as additional hydrogen bonding sites for water molecules.

The second sphere complexes of the present invention may be administered in any convenient manner to the subject. For example, the complexes may be dissolved in a saline solution and injected intravenously or subcutaneously. Generally, the dosages will be limited to only those amounts necessary and sufficient to allow detection by magnetic resonance imaging. Such dosages typically range from about 0.05 mmol kg$^{-1}$ to about 0.03 mmol kg$^{-1}$. Preferably, the dosages range from about 0.1 mmol kg$^{-1}$ to about 0.2 mmol kg$^{-1}$.

The second sphere complexes of the present invention enhance magnetic resonance imaging conducted utilizing conventional nuclear magnetic resonance devices. The complexes shorten the imaging time required to produce and maintain images of the target tissues.

EXAMPLES 1 and 2

Solutions are prepared containing the following substances for in vitro analysis by NMR:

Example 1

Varying concentrations of the tris(TIRON®)iron(III) complex under conditions of pH where the tris(ligand) complex, with no inner sphere water molecules, is essentially the only iron-containing species in solution. This complex has second-sphere water molecules coordinated to ligand sites.

Comparison 1

Varying concentrations of the Gd(III) complex of the ligand diethylenetriaminepentaacetic acid (DPTA). This is a complex marketed in solution under the trade name MAGNEVIST®, and is known through other studies to have one inner sphere water molecule.

Example 2

Varying concentrations of the tris(catecholate)iron(III) complex under conditions of pH where the tris(ligand) complex, with no inner sphere water molecules, is essentially the only iron-containing species in solution. This complex has second-sphere water molecules coordinated to ligand sites.

Comparison 2

Varying concentrations of the tris(ligand) iron(III) complex of 2,3-dihydroxynaphthalene, a derivative of catechol with hydrophobic groups attached to prevent second sphere coordination of water molecules, under conditions of pH where the tris(ligand) complex is essentially the only iron-containing species in solution. This complex has no second-sphere water molecules coordinated to ligand sites.

The solutions for Examples 1 and 2 are prepared in such a manner that a dose of 0.5 mL would deliver the appropriate amount of agent for the body weight of a subject, e.g. 0.1 mmol per kg of body weight. The pH of the solutions are adjusted to near-physiologic value (ca. 7.4) and the solutions are passed through a filtration device to remove particulate matter. A typical solution is prepared as follows: iron(III) nitrate (one equivalent) and disodium-1,2-dihydroxybenzene-3,5-disulfonate (three equivalents) are added together in distilled, deionized water. The pH is adjusted with hydrochloric acid and/or ammonium hydroxide to ca. 7.4 and the concentration of iron(III) adjusted to the desired level (such that, for example, 0.5 mL delivers 0.1 mmol per kg of body weight for the subject under investigation) with distilled, deionized water. Under these conditions, the iron(III) tris-(TIRON®) complex self-assembles with second sphere water molecules.

The Example and Comparison solutions are imaged in an MRI unit under conditions designed to explore differences caused by changes in longitudinal relaxation. Results of region-of-interest (ROI) measurements can be plotted against concentration to illustrate the effect of the different complexes on image brightness.

It is observed that Example 1 and Comparison 1 give about the same intensity maxima, despite the fact that the Gd(III) complex has one inner sphere water molecule and the Fe(III) complex has no inner sphere water molecules. Thus, the second sphere effect is evident for the Fe(III) complex.

Furthermore, it is observed that the maximum intensity for Comparison 2 is low in comparison to Example 2. The hydrophobic groups of the 2,3-dihydroxynaphthalene exclude second sphere water molecules in the solutions of Comparison 2, while the catechol complex Example 2 experiences second sphere coordination.

These results show that: (i) systems with inner sphere water molecules such as Gd(III)-DTPA, are effective; (ii) systems with no inner sphere waters and no second sphere waters, such as the Fe(III) tris(ligand) complex of 2,3-dihydroxynaphthalene, are not effective; and (iii) systems with no inner sphere waters but with second sphere waters, such as the Fe(III) tris(ligand) complexes of catechol and TIRON®, are effective.

EXAMPLE 3

To illustrate the utility of Fe(III) tironate as an MRI contrast agent, aqueous solutions of the second-sphere complex were prepared at a pH of ca. 7.4 and filtered. The aqueous solutions of the second-sphere complex were administered to anaesthetized male fisher rats in amounts of 0.05 mmol kg$^{-1}$, 0.10 mmol kg$^{-1}$ and 0 15 mmol kg$^{-1}$. The animals were imaged in the head coil of a conventional MRI unit with a pulse sequence designed to emphasize differences in $T_1$ ($T_1$ weighted sequence). The resulting images were analyzed numerically by region-of-interest (ROI) measurements on various organs. The intensity of the kidney image, as indicated by the ROI measurements, increases from ca. 300 arbitrary units for control animals with no contrast agent administered, to ca. 400 (0.05 mmol kg$^{-1}$) ca 500 (0.10 mmol kg$^{-1}$) and ca 600 (0.15 mmol kg$^{-1}$) as the dose is increased.

The resulting images on the liver showed similar, though less dramatic, effects. A higher dosage of the second-sphere complex (0.15 mmol kg$^{-1}$) is needed for a statistically significant increase in the ROI level. These results show that the second-sphere agent is capable of increasing image intensity of specific organs relative to background levels.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A second sphere contrast enhancing agent for magnetic resonance imaging of tissue, comprising a highly charged hydrophilic complex having a charge of three minus or greater which consists of a paramagnetic metal ion and at least one 1,2-dihydroxybenzene catecholate ligand coordinated to said paramagnetic metal ion.

2. The second sphere contrast enhancing agent according to claim 1, wherein the paramagnetic metal ion is selected from the group consisting of iron(III) and gadolinium(III).

3. The second sphere contrast enhancing agent according to claim 1, wherein the ligand is prepared from the salt disodium-1,2-dihydroxybenzene-3,5-disulfonate.

4. The second sphere contrast enhancing agent according to claim 1, wherein the paramagnetic metal ion is iron(III) and the ligand is prepared from the salt disodium-1,2-dihydroxybenzene-3,5-disulfonate.

5. The second sphere contrast enhancing agent according to claim 1, wherein the paramagnetic metal ion is gadolinium(III) and the ligand is prepared from the salt disodium-1,2-dihydroxybenzene-3,5-disulfonate.

6. A method for performing magnetic resonance imaging of a patient, comprising:
    a) providing a second sphere contrast enhancing agent, comprising a highly charged hydrophilic complex having a charge of three minus or greater which consists of a paramagnetic metal ion and at least one 1,2-dihydroxybenzene catecholate ligands coordinated thereto,
    b) administering the second sphere contrast enhancing agent to the patient;
    c) forming one or more hydrogen bonds between the paramagnetic metal ion-to-ligand linkage and tissue water molecules of the patient; and
    d) subjecting the patient to nuclear magnetic resonance imaging.

7. The method for performing magnetic resonance imaging of a patient according to claim 6, wherein the paramagnetic metal ion is selected from the group consisting of iron(III) and gadolinium(III).

8. The method for performing magnetic resonance imaging of a patient according to claim 6, wherein the ligand is prepared from the salt of disodium-1,2-dihydroxybenzene-3,5-disulfonate.

9. The method for performing magnetic resonance imaging of a patient according to claim 7, wherein the paramagnetic metal ion is iron(III) and the ligand is prepared from the salt disodium-1,2-dihydroxybenzene-3,5-disulfonate.

10. The method for performing magnetic resonance imaging of a patient according to claim 6, wherein the paramagnetic metal ion is gadolinium(III) and the ligand is prepared from the salt disodium-1,2-dihydroxybenzene-3,5-disulfonate.

11. A second sphere contrast enhancing agent for magnetic resortames imaging of tissue, comprising:
    a) a paramagnetic metal ion selected (III) and gadolinium (III);
    b) at least one 1,2-dihydroxybenzene catecholate ligand coordinated to said paramagnetic metal ion to form a highly charged hydrophilic complex having a charge of three minus or greater, said catecholate ligands prepared from the salt disodium-1,2-dihydroxybenzene-3,5-disulfonate end forming bonding sites for hydrogen bonding where such hydrogen bonding sites include heteroatoms which form paramagnetic metal ion-to-ligand linkages; and
    c) water molecules hydrogen bonded to the bonding sites of said catecholate ligands.

12. The second sphere contrast enhancing agent according to claim 11, wherein the bonding sites for hydrogen bonding said water molecules include the heteroatoms which form the paramagnetic metal ion-to-ligand linkages.

\* \* \* \* \*